US012718932B2

(12) United States Patent
Kanakatte Gurumurthy et al.

(10) Patent No.: US 12,718,932 B2
(45) Date of Patent: Aug. 25, 2026

(54) METHOD AND SYSTEM FOR MAGNETIC RESONANCE (MR) IMAGE ANALYSIS

(71) Applicant: Tata Consultancy Services Limited, Mumbai (IN)

(72) Inventors: Aparna Kanakatte Gurumurthy, Bangalore (IN); Pavan Kumar Reddy Kancham, Bangalore (IN); Jayavardhana Rama Gubbi Lakshminarasimha, Bangalore (IN); Avik Ghose, Kolkata (IN); Divya Manoharlal Bhatia, Bangalore (IN)

(73) Assignee: Tata Consultancy Services Limited, Mumbai (IN)

( * ) Notice: Subject to any disclaimer, the term of this patent is extended or adjusted under 35 U.S.C. 154(b) by 240 days.

(21) Appl. No.: 18/744,811

(22) Filed: Jun. 17, 2024

(65) Prior Publication Data

US 2025/0006346 A1 Jan. 2, 2025

(51) Int. Cl.

| | |
|---|---|
| ***G06V 10/82*** | (2022.01) |
| ***G06T 7/194*** | (2017.01) |
| ***G06V 10/24*** | (2022.01) |
| ***G06V 10/44*** | (2022.01) |

(Continued)

(52) U.S. Cl.

CPC ............. *G16H 30/40* (2018.01); *G06T 7/194* (2017.01); *G06V 10/24* (2022.01); *G06V 10/44* (2022.01); *G16H 30/20* (2018.01)

(58) Field of Classification Search

CPC ........ G16H 30/40; G16H 30/20; G06T 7/194; G06V 10/24; G06V 10/44; G06V 2201/03; G06V 10/82

See application file for complete search history.

(56) References Cited

U.S. PATENT DOCUMENTS

| | | | | |
|---|---|---|---|---|
| 10,600,184 | B2 * | 3/2020 | Golden | G06T 7/10 |
| 10,909,681 | B2 * | 2/2021 | Hsiao | G06N 3/045 |
| 10,910,099 | B2 * | 2/2021 | Xu | G06V 10/26 |

OTHER PUBLICATIONS

Liu et al., "Facial Landmark Detection Using Generative Adversarial Network Combined with Autoencoder for Occlusion," Mathematical Problems in Engineering, (2020).

(Continued)

*Primary Examiner* — Phuoc Tran

(74) *Attorney, Agent, or Firm* — Finnegan, Henderson, Farabow, Garrett & Dunner, LLP

(57) ABSTRACT

Existing Magnetic Resonance (MR) analysis approaches are either manual, which is time consuming and error prone, or automatic yet fail to identify correct landmarks. The disclosure herein generally relates method and system for MR image analysis. The system trains and uses a Generative adversarial network (GAN) for the MR image analysis. A generator network of the GAN generates a heatmap of a plurality of landmarks, by processing input data. Further, a discriminator network of the GAN, which has gradients updated based on a Modified Discriminator Loss (MDL) calculated based on a foreground pixel loss function and a standard discriminator loss, predicts each of a plurality of patches in a second input data as one of real and fake, based on presence of the one or more foreground pixel regions in the landmark heatmap in the ground-truth heatmap identified based on the foreground pixel loss function.

17 Claims, 8 Drawing Sheets

(51) Int. Cl.
*G16H 30/20* (2018.01)
*G16H 30/40* (2018.01)

(56) References Cited

OTHER PUBLICATIONS

Neff et al., "Generative Adversarial Network based Synthesis for Supervised Medical Image Segmentation," (2017).
Payer et al., "Regressing Heatmaps for Multiple Landmark Localization using CNNs," (2016).
Shin et al., "GANDALF: Generative Adversarial Networks with Discriminator-Adaptive Loss Fine-tuning for Alzheimer's Disease Diagnosis from MRI," (2020).
Son et al., "Towards Accurate Segmentation of Retinal Vessels and the Optic Disc in Fundoscopic Images with Generative Adversarial Networks," Journal of Digital Imaging, 32:499-512 (2019).

* cited by examiner

302 identifying, via the one or more hardware processors, one or more foreground pixel regions in the ground-truth heatmap, wherein the one or more foreground pixel regions are patches having coverage of foreground pixels exceeding a threshold of coverage, in the ground-truth heatmap

304 calculating, via the one or more hardware processors, value of the foreground pixel loss function, for the identified one or more foreground pixel regions in the ground-truth heatmap

METHOD AND SYSTEM FOR MAGNETIC RESONANCE (MR) IMAGE ANALYSIS

PRIORITY CLAIM

This U.S. patent application claims priority under 35 U.S.C. § 119 to: Indian patent application No. 202321043069, filed on Jun. 27, 2023. The entire contents of the aforementioned application are incorporated herein by reference.

TECHNICAL FIELD

The disclosure herein generally relates to Magnetic Resonance (MR) imaging, and, more particularly, to a method and system for MR image analysis.

BACKGROUND

Magnetic resonance imaging, or MRI, is a noninvasive medical imaging test that produces detailed images of almost every internal structure in the human body, including the organs, bones, muscles and blood vessels. MRI scanners create images of the body using a large magnet and radio waves. For accurate disease diagnostics, it is important that MRI output is of desired quality. For example, in cardiology, precise information on both the dimensions and functions of the heart chambers is essential in clinical applications for diagnosis, prognosis, and therapeutic decisions. Cardiac MR is considered the gold standard for the non-invasive characterization of cardiac function, primarily due to its high spatial resolution and 3D capabilities. It has proven to be an invaluable tool for the diagnosis of complex cardiomyopathies.

While the MR imaging technologies have rapidly advanced with the advent of technology, image analysis and interpretation of MR images are time-consuming and error-prone due to the involvement of human operators. Reliable anatomical landmark detection is an important first step for many medical imaging algorithms. A landmark or local feature is a specific image location that serves as a fixed reference. Local features can be corners, edges, or image regions. Particularly in medical imaging, these landmark points act as individual anchor points that help in interpreting the image and understanding the location of one anatomical structure in relation to another.

These landmarks can be used in registration, motion tracking, segmentation, building 3D models, and other applications. These landmarks facilitate robust and precise functional and structural analysis of the heart and also helps in accurate surgical pre-planning. However, accurate automatic detection of landmarks in medical images is challenging due to anatomical variation among patients and also differences in image acquisition. In clinical practice, manual delineation by cardiologists remains the main approach to quantifying cardiac function.

Learning-based object detection approaches have been demonstrated successfully in many applications. However, they still encounter challenges in a cluttered environment, such as landmark detection in cardiac MR long-axis slices, due to large anatomy shape and appearance variations across populations along with different acquisition parameters. Several organs in the body in addition to the heart appear in the same slice. For the same patient, time sampling across the entire heartbeat cycle, with end-systole and end-diastole as two ends, also leads to significantly different myocardium contour shape changes. These variations and ambiguities result in challenges for each landmark detector to identify correct landmarks. The need for accurately detecting the landmarks is very crucial for medical applications as a few pixel error maps to very high millimeters, which can alter the outcome of surgical procedures.

SUMMARY

Embodiments of the present disclosure present technological improvements as solutions to one or more of the above-mentioned technical problems recognized by the inventors in conventional systems. For example, in one embodiment, a processor implemented method is provided. The method includes receiving, via one or more hardware processors, one or more Magnetic Resonance (MR) images, as a first input data, by a Generative adversarial network (GAN), wherein the one or more MR images may comprise images with or without anomalies. Further, pre-processing of the first input data is performed, via the one or more hardware processors, to generate a pre-processed data. Further, a 3D data augmentation is performed dynamically on the pre-processed data, via the one or more hardware processors, to generate an augmented data. Further, a heatmap of a plurality of landmarks in the one or more MR images is obtained, via the one or more hardware processors, by processing the augmented data using a generator network of the GAN. Further, value of a Foreground Pixel Loss (FPL) function, and a second input data are fed to a discriminator network of the GAN, via the one or more hardware processors, wherein the second input data comprises a) an original image and the obtained landmark heatmap from the generator network, and b) the original image and an associated ground-truth heatmap. Further, gradients of the discriminator network are updated, via the one or more hardware processors, based on value of a Modified Discriminator Loss (MDL), wherein the MDL is obtained as a combination of the FPL and a Standard Discriminator Loss (SDL) of the discriminator network. Further, one or more patches in the obtained landmark heatmap are identified using the discriminator network, via the one or more hardware processors, as associated with the ground-truth heatmap, based on the updated gradients. Further, each of a plurality of patches in the second input data is predicted as one of real and fake, using the discriminator network, via the one or more hardware processors, based on the one or more patches in the obtained landmark heatmap identified as associated with the ground-truth heatmap.

In an embodiment of the method, performing the pre-processing of the first input data comprises performing a) an image orientation normalization, b) generating a single gaussian heatmap image for each of the plurality of landmarks, c) normalizing by applying zero padding, d) normalizing pixel values, and e) generating a heatmap image comprising all of the plurality of landmarks.

In another embodiment of the method, wherein the generator network comprises of an encoder and a decoder with a plurality of skip connections along with a feature-filter enhancing block, wherein, a plurality of key features of each of the one or more MR images is represented as vectors in latent space by the encoder, a plurality of up-sampled vectors in a decoder path are concatenated with symmetrically opposite output vector in an encoder path along a channel axis, using the plurality of skip connections, a plurality of features from a down-sampled encoder layer are concatenated using the feature-filter enhancing block, and a heat map comprising of a pixel spread normalized in a defined range is generated.

In another embodiment of the method, a generative loss of the generator network is represented as $$G_L = A_L + \beta * L_L,$$

where, $A_L$ is an adversary loss, β is an intensity parameter, and $L_L$ is a learning loss.

In another embodiment of the method, the learning loss is computed as $$L_L = Huber(GT_h, GP_h, \delta = 0.4),$$

where, $GP_h$ is the heatmap obtained by the generator network, and $GT_h$ is the ground-truth heatmap.

In another embodiment of the method, the foreground pixel loss function is computed as $$FPL = \propto * MSE(P_1, P_2) + MAE(P_1, P_2),$$

where, $P_1$ is a ground truth patch, $P_2$ is a predicted patch, ∝ is a regularization parameter, MAE is Mean Absolute Error, and MSE is Mean Square Error.

In another embodiment of the method, the discriminator network comprises of a plurality of sequentially arranged 2D convolution layers.

In another embodiment of the method, the value of the FPL function is obtained by identifying, via the one or more hardware processors, one or more foreground pixel regions in the ground-truth heatmap, wherein the one or more foreground pixel regions are patches having coverage of foreground pixels exceeding a threshold of coverage, in the ground-truth heatmap; and calculating, via the one or more hardware processors, value of the foreground pixel loss function, for the identified one or more foreground pixel regions in the ground-truth heatmap.

In yet another embodiment, a system is provided. The system includes one or more hardware processors, a communication interface, and a memory storing a plurality of instructions. The plurality of instructions cause the one or more hardware processors to receive one or more Magnetic Resonance (MR) images, as a first input data, by a Generative adversarial network (GAN), wherein the one or more MR images may comprise images with or without anomalies. Further, pre-processing of the first input data is performed, via the one or more hardware processors, to generate a pre-processed data. Further, a 3D data augmentation is performed dynamically on the pre-processed data, via the one or more hardware processors, to generate an augmented data. Further, a heatmap of a plurality of landmarks in the one or more MR images is obtained, via the one or more hardware processors, by processing the augmented data using a generator network of the GAN. Further, value of a Foreground Pixel Loss (FPL) function, and a second input data are fed to a discriminator network of the GAN, via the one or more hardware processors, wherein the second input data comprises a) an original image and the obtained landmark heatmap from the generator network, and b) the original image and an associated ground-truth heatmap. Further, gradients of the discriminator network are updated, via the one or more hardware processors, based on value of a Modified Discriminator Loss (MDL), wherein the MDL is obtained as a combination of the FPL and a Standard Discriminator Loss (SDL) of the discriminator network. Further, one or more patches in the obtained landmark heatmap are identified using the discriminator network, via the one or more hardware processors, as associated with the ground-truth heatmap, based on the updated gradients. Further, each of a plurality of patches in the second input data is predicted as one of real and fake, using the discriminator network, via the one or more hardware processors, based on the one or more patches in the obtained landmark heatmap identified as associated with the ground-truth heatmap.

In yet an embodiment of the system, performing the pre-processing of the first input data comprises performing a) an image orientation normalization, b) generating a single gaussian heatmap image for each of the plurality of landmarks, c) normalizing by applying zero padding, d) normalizing pixel values, and e) generating a heatmap image comprising all of the plurality of landmarks.

In yet another embodiment of the system, wherein the generator network comprises of an encoder and a decoder with a plurality of skip connections along with a feature-filter enhancing block, wherein, a plurality of key features of each of the one or more MR images is represented as vectors in latent space by the encoder, a plurality of up-sampled vectors in a decoder path are concatenated with symmetrically opposite output vector in an encoder path along a channel axis, using the plurality of skip connections, a plurality of features from a down-sampled encoder layer are concatenated using the feature-filter enhancing block, and a heat map comprising of a pixel spread normalized in a defined range is generated.

In yet another embodiment of the system, a generative loss of the generator network is represented as $$G_L = A_L + \beta * L_L,$$

where, $A_L$ is an adversary loss, β is an intensity parameter, and $L_L$ is a learning loss.

In yet another embodiment of the system, the learning loss is computed as $$L_L = Huber(GT_h, GP_h, \delta = 0.4),$$

where, $GP_h$ is the heatmap obtained by the generator network, and $GT_h$ is the ground-truth heatmap.

In yet another embodiment of the system, the foreground pixel loss function is computed as $$FPL = \propto * MSE(P_1, P_2) + MAE(P_1, P_2),$$

where, $P_1$ is a ground truth patch, $P_2$ is a predicted patch, ∝ is a regularization parameter, MAE is Mean Absolute Error, and MSE is Mean Square Error.

In yet another embodiment of the system, the discriminator network comprises of a plurality of sequentially arranged 2D convolution layers.

In yet another embodiment of the system, the value of the FPL function is obtained by identifying, via the one or more hardware processors, one or more foreground pixel regions in the ground-truth heatmap, wherein the one or more foreground pixel regions are patches having coverage of foreground pixels exceeding a threshold of coverage, in the ground-truth heatmap; and calculating, via the one or more hardware processors, value of the foreground pixel loss function, for the identified one or more foreground pixel regions in the ground-truth heatmap.

In yet another embodiment, a non-transitory computer readable medium is provided. The non-transitory computer readable medium includes a plurality of instructions, which when executed, cause the one or more hardware processors to receive, via one or more hardware processors, one or more Magnetic Resonance (MR) images, as a first input data, by a Generative adversarial network (GAN), wherein the one or more MR images may comprise images with or without anomalies. Further, pre-processing of the first input data is performed, via the one or more hardware processors, to generate a pre-processed data. Further, a 3D data augmentation is performed dynamically on the pre-processed data, via the one or more hardware processors, to generate an augmented data. Further, a heatmap of a plurality of landmarks in the one or more MR images is obtained, via the one or more hardware processors, by processing the augmented data using a generator network of the GAN. Further, value of a Foreground Pixel Loss (FPL) function, and a second input data are fed to a discriminator network of the GAN, via the one or more hardware processors, wherein the second input data comprises a) an original image and the obtained landmark heatmap from the generator network, and b) the original image and an associated ground-truth heatmap. Further, gradients of the discriminator network are updated, via the one or more hardware processors, based on value of a Modified Discriminator Loss (MDL), wherein the MDL is obtained as a combination of the FPL and a Standard Discriminator Loss (SDL) of the discriminator network. Further, one or more patches in the obtained landmark heatmap are identified using the discriminator network, via the one or more hardware processors, as associated with the ground-truth heatmap, based on the updated gradients. Further, each of a plurality of patches in the second input data is predicted as one of real and fake, using the discriminator network, via the one or more hardware processors, based on the one or more patches in the obtained landmark heatmap identified as associated with the ground-truth heatmap.

In an embodiment of the non-transitory computer readable medium, performing the pre-processing of the first input data comprises performing a) an image orientation normalization, b) generating a single gaussian heatmap image for each of the plurality of landmarks, c) normalizing by applying zero padding, d) normalizing pixel values, and e) generating a heatmap image comprising all of the plurality of landmarks.

In another embodiment of the non-transitory computer readable medium, wherein the generator network comprises of an encoder and a decoder with a plurality of skip connections along with a feature-filter enhancing block, wherein, a plurality of key features of each of the one or more MR images is represented as vectors in latent space by the encoder, a plurality of up-sampled vectors in a decoder path are concatenated with symmetrically opposite output vector in an encoder path along a channel axis, using the plurality of skip connections, a plurality of features from a down-sampled encoder layer are concatenated using the feature-filter enhancing block, and a heat map comprising of a pixel spread normalized in a defined range is generated.

In another embodiment of the non-transitory computer readable medium, a generative loss of the generator network is represented as $$G_L = A_L + \beta * L_L,$$

where, $A_L$ is an adversary loss, β is an intensity parameter, and $L_L$ is a learning loss.

In another embodiment of the non-transitory computer readable medium, the learning loss is computed as $$L_L = Huber(GT_h, GP_h, \delta = 0.4),$$

where, $GP_h$ is the heatmap obtained by the generator network, and $GT_h$ is the ground-truth heatmap.

In another embodiment of the non-transitory computer readable medium, the foreground pixel loss function is computed as $$FPL = \propto * MSE(P_1, P_2) + MAE(P_1, P_2),$$

where, $P_1$ is a ground truth patch, $P_2$ is a predicted patch, ∝ is a regularization parameter, MAE is Mean Absolute Error, and MSE is Mean Square Error.

In another embodiment of the non-transitory computer readable medium, the discriminator network comprises of a plurality of sequentially arranged 2D convolution layers.

In another embodiment of the non-transitory computer readable medium, the value of the FPL function is obtained by identifying, via the one or more hardware processors, one or more foreground pixel regions in the ground-truth heatmap, wherein the one or more foreground pixel regions are patches having coverage of foreground pixels exceeding a threshold of coverage, in the ground-truth heatmap; and calculating, via the one or more hardware processors, value of the foreground pixel loss function, for the identified one or more foreground pixel regions in the ground-truth heatmap.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

Figure 3:
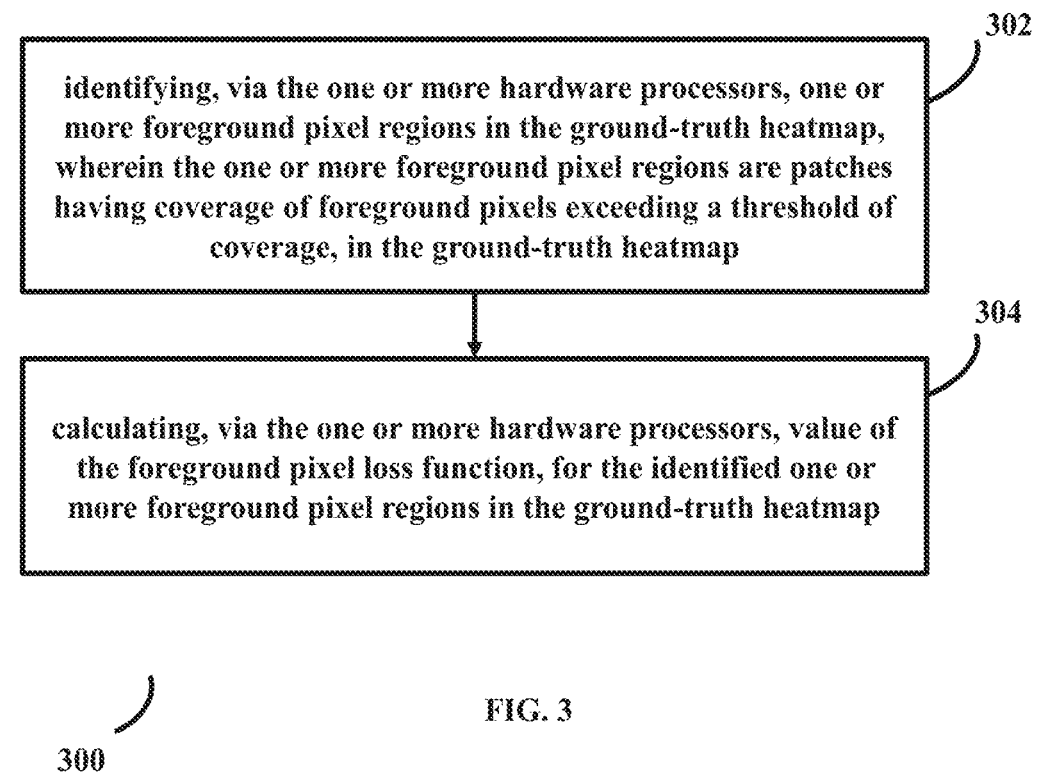

FIG. 3 illustrates a flow diagram depicting steps involved in the process of obtaining value of Foreground Pixel Loss (FPL) function, by the system of FIG. 1, according to some embodiments of the present disclosure.

DETAILED DESCRIPTION

Figure 1:
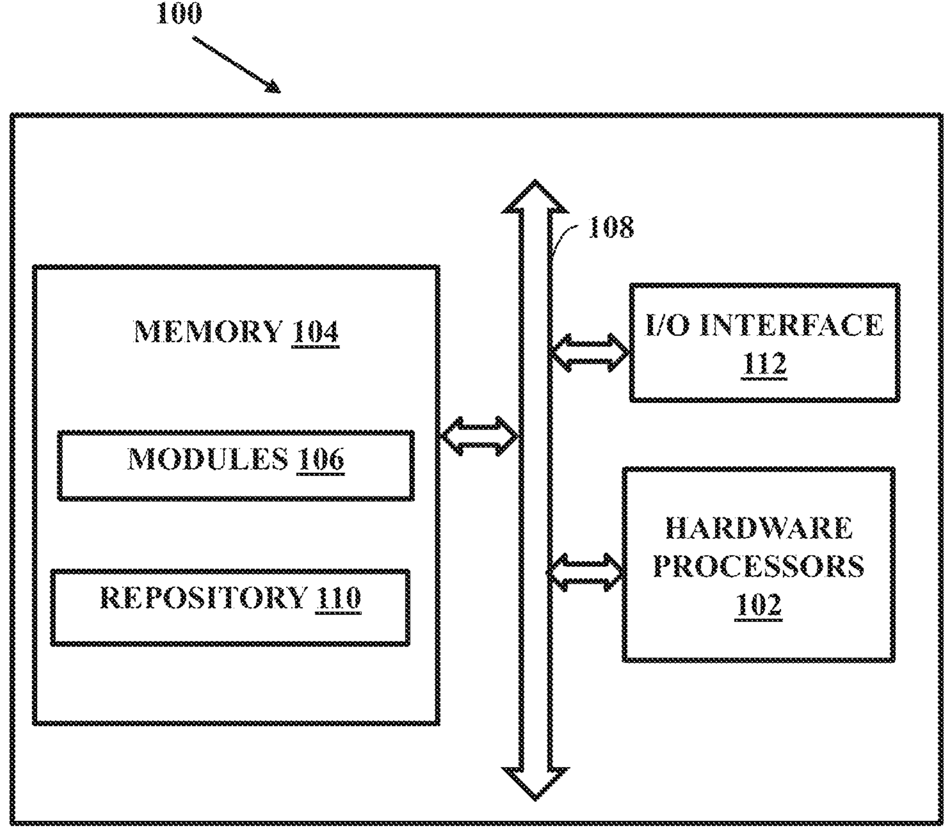
FIG. 1 illustrates an exemplary system for Magnetic Resonance (MR) image analysis, according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Landmark detection is required to be performed as part of Magnetic Resonance (MR) image analysis. The landmarks can be used in registration, motion tracking, segmentation, building 3D models, and other applications. These landmarks facilitate robust and precise functional and structural analysis of the heart and also helps in accurate surgical pre-planning. However, accurate automatic detection of landmarks in medical images is challenging due to anatomical variation among patients and also differences in image acquisition. For example, in cardiology domain, manual delineation by cardiologists remains the main approach to quantifying cardiac function, which is time consuming and error prone approach.

Learning-based object detection approaches have been demonstrated successfully in many applications. However, they still encounter challenges in a cluttered environment, such as landmark detection in cardiac MR long-axis slices, due to large anatomy shape and appearance variations across populations along with different acquisition parameters. Several organs in the body in addition to the heart appear in the same slice. For the same patient, time sampling across the entire heartbeat cycle, with end-systole and end-diastole as two ends, also leads to significantly different myocardium contour shape changes. These variations and ambiguities result in challenges for each landmark detector to identify correct landmarks. The need for accurately detecting the landmarks is very crucial for medical applications as a few pixel error maps to very high millimeters which can alter the outcome of surgical procedures.

In order to address these challenges, embodiments disclosed herein provide a method and system for MR image analysis. The method includes receiving one or more Magnetic Resonance (MR) images, as a first input data, by a Generative adversarial network (GAN), wherein the one or more MR images may comprise images with or without anomalies. Further, pre-processing of the first input data is performed to generate a pre-processed data. Further, a 3D data augmentation is performed dynamically on the pre-processed data to generate an augmented data. Further, a heatmap of a plurality of landmarks in the one or more MR images is obtained by processing the augmented data using a generator network of the GAN. Further, value of a Foreground Pixel Loss (FPL) function, and a second input data are fed to a discriminator network of the GAN, wherein the second input data comprises a) an original image and the obtained landmark heatmap from the generator network, and b) the original image and an associated ground-truth heatmap. Further, gradients of the discriminator network are updated based on value of a Modified Discriminator Loss (MDL), wherein the MDL is obtained as a combination of the FPL and a Standard Discriminator Loss (SDL) of the discriminator network. Further, one or more patches in the obtained landmark heatmap are identified using the discriminator network, as associated with the ground-truth heatmap, based on the updated gradients. Further, each of a plurality of patches in the second input data is predicted as one of real and fake, using the discriminator network, based on the one or more patches in the obtained landmark heatmap identified as associated with the ground-truth heatmap.

Referring now to the drawings, and more particularly to FIG. 1 through FIG. 8, where similar reference characters denote corresponding features consistently throughout the figures, there are shown preferred embodiments and these embodiments are described in the context of the following exemplary system and/or method.

FIG. 1 illustrates an exemplary system for Magnetic Resonance (MR) image analysis, according to some embodiments of the present disclosure.

The system 100 includes or is otherwise in communication with hardware processors 102, at least one memory such as a memory 104, an I/O interface 112. The hardware processors 102, memory 104, and the Input/Output (I/O) interface 112 may be coupled by a system bus such as a system bus 108 or a similar mechanism. In an embodiment, the hardware processors 102 can be one or more hardware processors.

The I/O interface 112 may include a variety of software and hardware interfaces, for example, a web interface, a graphical user interface, and the like. The I/O interface 112 may include a variety of software and hardware interfaces, for example, interfaces for peripheral device(s), such as a keyboard, a mouse, an external memory, a printer and the like. Further, the I/O interface 112 may enable the system 100 to communicate with other devices, such as web servers, and external databases.

The I/O interface 112 can facilitate multiple communications within a wide variety of networks and protocol types, including wired networks, for example, local area network (LAN), cable, etc., and wireless networks, such as Wireless LAN (WLAN), cellular, or satellite. For the purpose, the I/O interface 112 may include one or more ports for connecting several computing systems with one another or to another server computer. The I/O interface 112 may include one or more ports for connecting several devices to one another or to another server.

The one or more hardware processors 102 may be implemented as one or more microprocessors, microcomputers, microcontrollers, digital signal processors, central processing units, node machines, logic circuitries, and/or any devices that manipulate signals based on operational instructions. Among other capabilities, the one or more hardware processors 102 is configured to fetch and execute computer-readable instructions stored in the memory 104.

The memory 104 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes. In an embodiment, the memory 104 includes a plurality of modules 106.

The plurality of modules 106 include programs or coded instructions that supplement applications or functions performed by the system 100 for executing different steps involved in the process of MR image analysis, being performed by the system 100. The plurality of modules 106, amongst other things, can include routines, programs, objects, components, and data structures, which performs particular tasks or implement particular abstract data types. The plurality of modules 106 may also be used as, signal processor(s), node machine(s), logic circuitries, and/or any other device or component that manipulates signals based on operational instructions. Further, the plurality of modules 106 can be used by hardware, by computer-readable instructions executed by the one or more hardware processors 102, or by a combination thereof. The plurality of modules 106 can include various sub-modules (not shown). The plurality of modules 106 may include computer-readable instructions that supplement applications or functions performed by the system 100 for the MR image analysis.

The data repository (or repository) 110 may include a plurality of abstracted piece of code for refinement and data that is processed, received, or generated as a result of the execution of the plurality of modules in the module(s) 106.

Although the data repository 110 is shown internal to the system 100, it will be noted that, in alternate embodiments, the data repository 110 can also be implemented external to the system 100, where the data repository 110 may be stored within a database (repository 110) communicatively coupled to the system 100. The data contained within such external database may be periodically updated. For example, new data may be added into the database (not shown in FIG. 1) and/or existing data may be modified and/or non-useful data may be deleted from the database. In one example, the data may be stored in an external system, such as a Lightweight Directory Access Protocol (LDAP) directory and a Relational Database Management System (RDBMS). Functions of the components of the system 100 are now explained with reference to the steps in flow diagrams in FIGS. 2 and 3, the block diagrams in FIG. 4, FIG. 5, and FIG. 6, and the example diagrams in FIGS. 7 and 8.

Figure 2A:
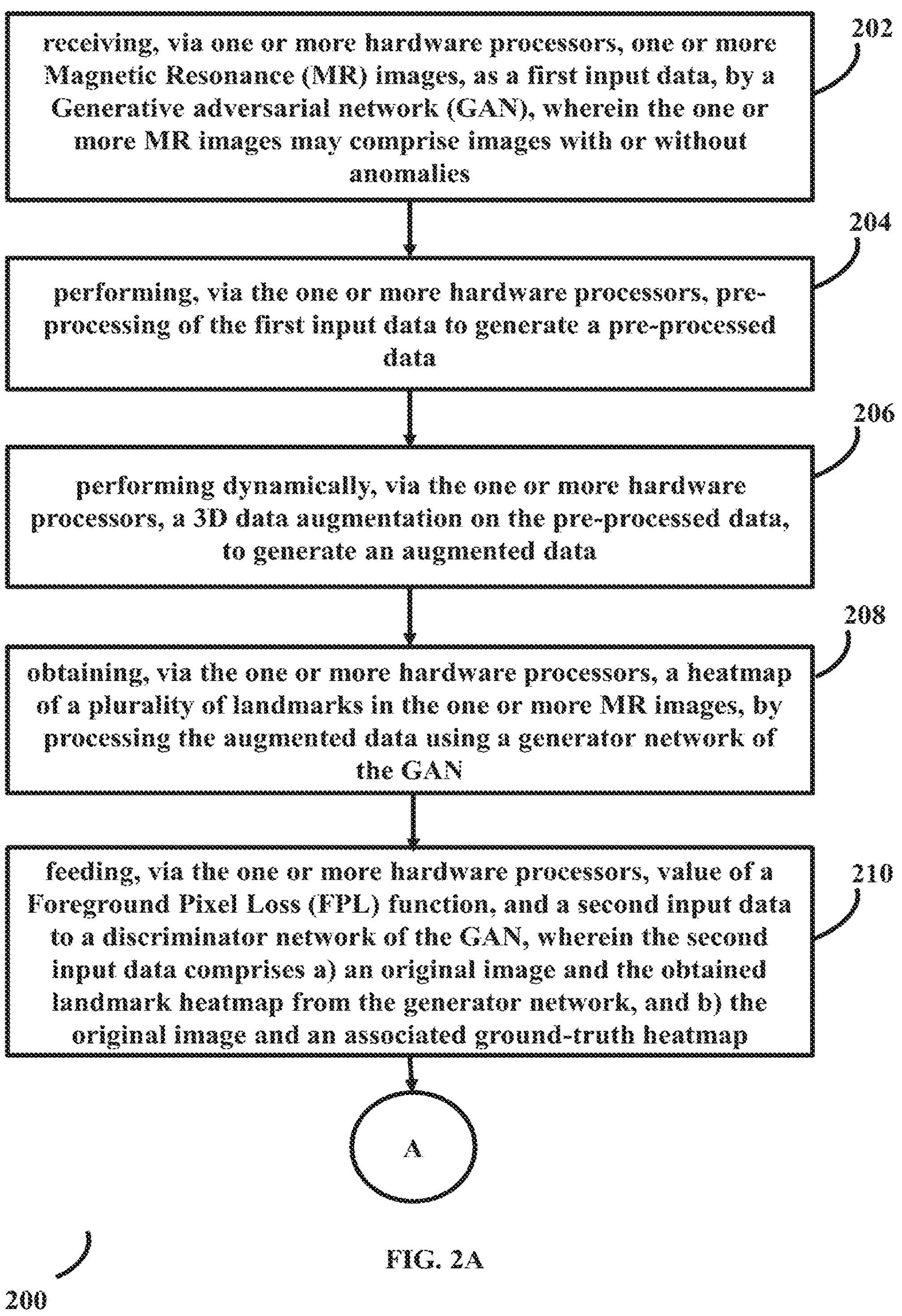
FIGS. 2A and 2B (alternately referred to as FIG. 2) illustrate a flow diagram depicting steps involved in the MR image analysis, by the system of FIG. 1, according to some embodiments of the present disclosure.
Figure 2B:
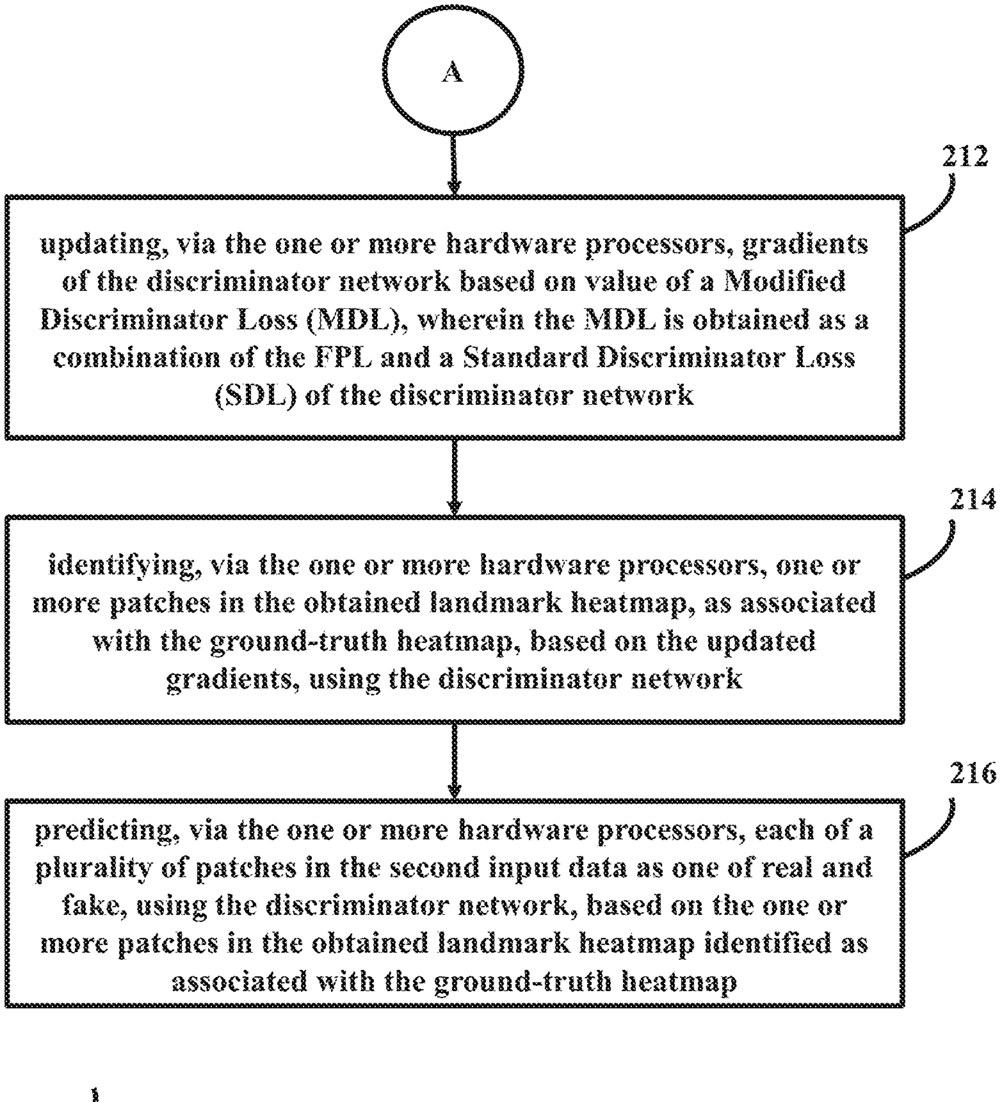

FIGS. 2A and 2B (alternately referred to as FIG. 2) illustrate a flow diagram depicting steps involved in the MR image analysis, by the system of FIG. 1, according to some embodiments of the present disclosure.

In an embodiment, the system 100 comprises one or more data storage devices or the memory 104 operatively coupled to the processor(s) 102 and is configured to store instructions for execution of steps of the method 200 by the processor(s) or one or more hardware processors 102. The steps of the method 200 of the present disclosure will now be explained with reference to the components or blocks of the system 100 as depicted in FIG. 1 and the steps of flow diagram as depicted in FIG. 2. Although process steps, method steps, techniques or the like may be described in a sequential order, such processes, methods, and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

Figure 4:
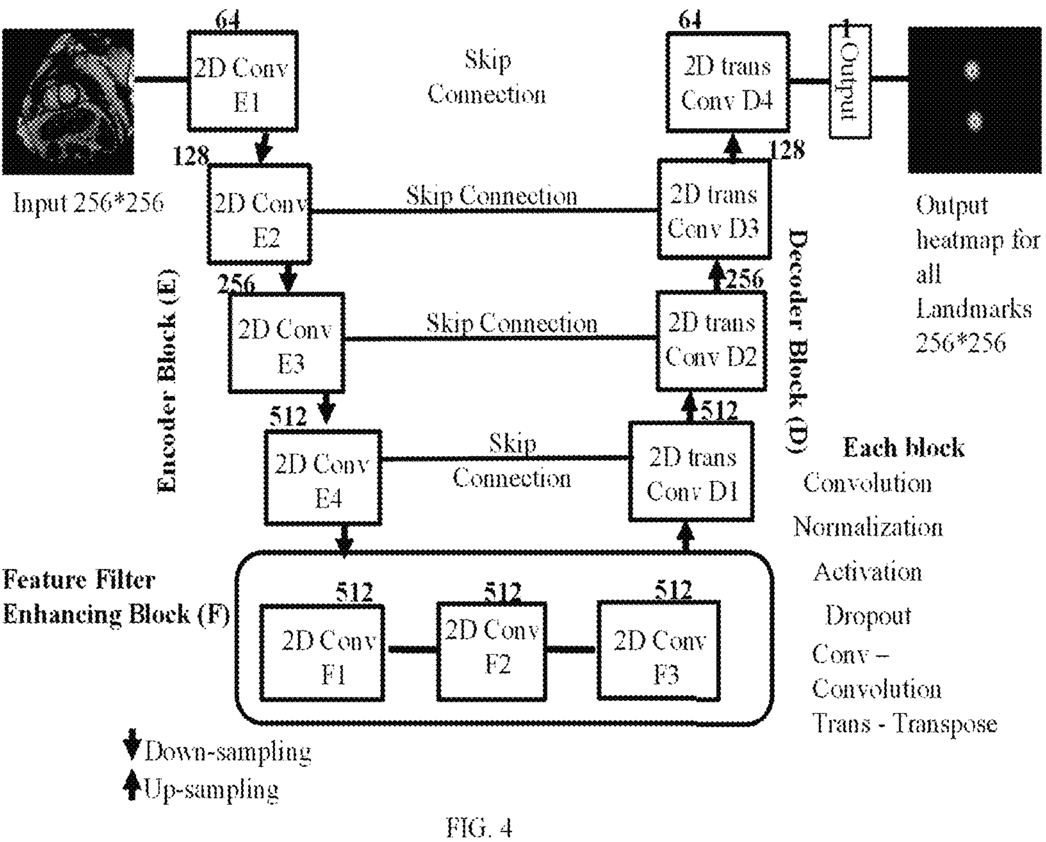
FIG. 4 depicts a block diagram of a generator network of a GAN network of the system of FIG. 1, in accordance with some embodiments of the present disclosure.
Figure 5:
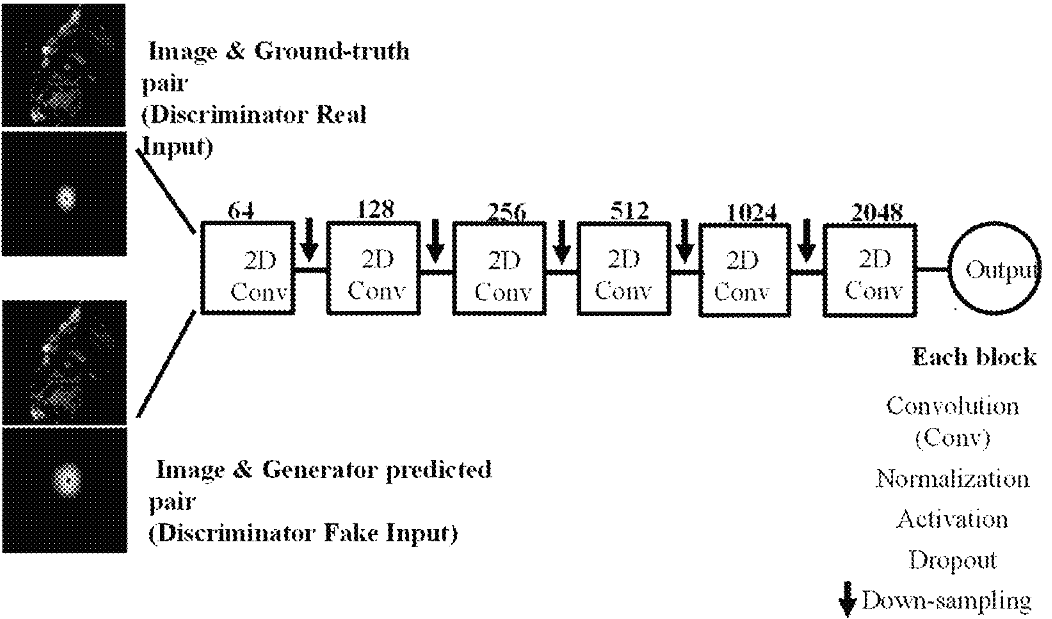
FIG. 5 depicts block diagram of a discriminator network of the GAN network of the system of FIG. 1 according to some embodiments of the present disclosure.

The system 100 uses a Generative adversarial network (GAN) for the MR image analysis. The GAN includes two neutral networks, i.e. a generator network and a discriminator network. In an embodiment, working of the GAN network is explained with reference to a cardiac MR image analysis. However, a person skilled in the art would appreciate that the embodiments disclosed herein are not intended to restrict use of the GAN network for MR image processing in application other than the cardiac signal processing. The generator network includes an encoder and a decoder, with skip connections and a feature filter enhancing block, as depicted in FIG. 4. The encoder represents key features from the input image as vectors in latent space. Skip connection concatenates the up-sampled vector in the decoder path with the symmetrically opposite output vector in the encoder path along the channel axis. The feature-filter enhancing block concatenates the features from down-sampled encoder layer. This helps in decreasing the parameters, avoiding the vanishing gradients, minimizing the plausibility of overfitting and also in preserving the lost features during down-sampling thereby retaining the specific and crucial information for increased accuracy.

At step 202 of method 200, a Generative adversarial network (GAN) of the system 100 receives, via the one or more hardware processors 102, one or more Magnetic Resonance (MR) images with anomalies, as a first input data. The GAN may receive the one or more MR images automatically from one or more associated data sources, for example, a hospital network, or may provide a user interface for one or more authorized users to manually feed the one or more MR images to the GAN. In various embodiments, the anomalies in the one or more MR images, collected at an instance, maybe of the same type, i.e. disease.

Further, at step 204 of the method 200, the system 100 performs pre-processing of the first input data, via the one or more hardware processors 102, to generate a pre-processed data. Performing the pre-processing of the first input data includes performing a) an image orientation normalization, b) generating a single gaussian heatmap image for each of the plurality of landmarks, c) normalizing by applying zero padding, d) normalizing pixel values, and e) generating a ground truth heatmap image comprising all of the plurality of landmarks of the induvial landmarks, and any other similar step as may be required. The ground truth heat map image thus includes heatmap of all of the landmarks in the first input data. Here, heatmap is a continuous pixel spread normalized in the range 0-1, having a Gaussian distribution with the mean centered along (α, β) as landmark coordinate points and variance. The gaussian heatmap is generated as:

$$H(x, y) = \frac{\exp\left(-(x-\alpha)^2 + (y-\beta)^2\right)}{2\sigma^2} \quad (1)$$

where, x, y are coordinates of the heatmap.

Further, at step 206 of the method 200, the system 100 dynamically performs a 3D data augmentation on the pre-processed data, via the one or more hardware processors 102, to generate an augmented data. The system 100 may use any suitable data augmentation technique, and may perform one or more of flipping, rotation, scaling, brightness adjustment, elastic deformation, and so on, on the pre-processed data.

Further, at step 208 of the method 200, the generator network generates a heatmap of a plurality of landmarks in the one or more MR images, via the one or more hardware processors, by processing the augmented data. The generator network takes the one or more MR images as input, and outputs the heatmap of the landmarks. The heatmap is a continuous pixel spread normalized in 0-1 range. Every landmark point is convolved with a Gaussian kernel of a specific standard deviation, and resulting distribution represents spatial probability of the landmark. A generative loss of the generator network is represented as $$G_L = A_L + \beta * L_L, \tag{2}$$

where, $A_L$ is an adversary loss, β is an intensity parameter, and $L_L$ is a learning loss.

$$A_L = MSE(I, GP_h) \tag{3}$$

$$L_L = H_{uber}(GT_h, GP_h, \delta = 0.4), \tag{4}$$

where, I is input image, $GP_h$ is generator predicted heatmap, $GT_h$ is ground truth based heatmap, and MSE is Mean Square Error. The Huber loss allows to combine good properties of both MSE and MAE (mean absolute error) thus making it less sensitive to outliers in data than squared error loss.

The discriminator network of the GAN includes a plurality of 2D convolution layers with parameters similar to the encoder of the generator network. Structure of the discriminator network is depicted in FIG. 4. At step 210 of the method 200, value of a Foreground Pixel Loss (FPL) function, and a second input data are fed, via the one or more hardware processors, to the discriminator network. The second input data includes a) an original image and the predicted landmark heatmap from the generator network, and b) the original image and the ground-truth heatmap.

In the second input data that is fed to the discriminator network, majority of pixels maybe in background when it comes to small object detection and foreground pixels that actually contribute to deciding may be very few. This makes the discriminator network pass the image or patch as true even if the foreground/key pixels are missing or in wrong location. The FPL function is used to address this problem. Steps involved in obtaining value of Foreground Pixel Loss (FPL) function are depicted in method 300 in FIG. 3, and are explained hereafter. At step 302 of the method 300, one or more foreground pixel regions in the ground-truth heatmap are identified, via the one or more hardware processors 102, wherein the one or more foreground pixel regions are patches having coverage of foreground pixels exceeding a threshold of coverage, in the ground-truth heatmap. In various embodiments, value of the threshold of coverage maybe statically or dynamically determined. Further, at step 304 of the method 200, value of the foreground pixel loss (FPL) function is calculated, via the one or more hardware processors 102, for the identified one or more foreground pixel regions in the ground-truth heatmap, as:

$$FPL = \propto * MSE(P_1, P_2) + MAE(P_1, P_2), \tag{5}$$

where, $P_1$ is a ground truth patch, $P_2$ is a predicted patch, ∝ is a regularization parameter, MAE is Mean Absolute Error, and MSE is Mean Square Error. By using both MAE and MSE, the discriminator network maintains a tradeoff between handling outliers and penalizing big error terms using equally weighted normalized mean loss function of both MSE and MAE.

Referring back to the method 200, at step 212, gradients of the discriminator network are updated based on value of a Modified Discriminator Loss (MDL), wherein the MDL is obtained as a combination of the FPL and a Standard Discriminator Loss (SDL) of the discriminator network.

$$\text{i.e., } MDL = SDL + FPL, \tag{6}$$

where, $$SDL = 0.5 * (DRL + DFL), \tag{7}$$

Where, $$\text{Discriminator Real Loss } (DRL) = MSE(I, GT_h) \tag{8}$$

$$\text{Discriminator Fake Loss } (DFL) = MSE(I, GP_h) \tag{9}$$

Figure 6:
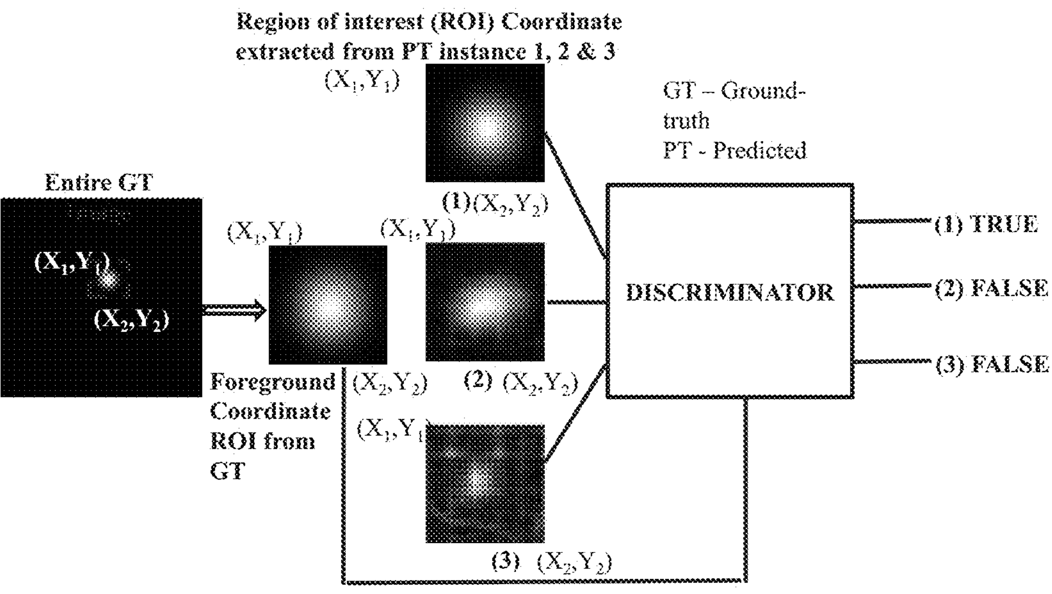
FIG. 6 depicts is foreground pixel loss function approach in the discriminator network, in accordance with some embodiments of the present disclosure.

Further, at step 214 of the method 200, the discriminator network identifies one or more patches in the obtained landmark heatmap, as associated with the ground-truth heatmap, based on the updated gradients. The FPL function identifies the foreground pixels of the landmark heatmap in the ground truth heatmap data, and creates a square bounding box ($X_1$, $Y_1$ and $X_2$, $Y_2$) patch, as depicted in FIG. 6. In an embodiment, the size of the patch is dynamically determined in run time.

Further, at step 216 of the method 200, the discriminator network predicts each of a plurality of patches in the second input data is predicted as one of real and fake, via the one or more hardware processors 102, based on the identified presence of the one or more foreground pixel regions in the landmark heatmap in the ground-truth heatmap.

Results and Discussions

For the experiments conducted, STACOM LV landmark detection challenge 2012 dataset was used as training data. The training data consisted of 100 patients images acquired in both the long and short-axis views. Data of 80 patients was for training and that of the remaining 20 patients were used for testing. Cross-validation was performed to ensure every patient data is part of training and testing at different stages. The dataset had 6 distinct landmark annotations as explained below. All the points were annotated by an experienced analyst. Mitral valve (MV) points: MV separates left atrium (LA) and the left ventricle (LV). This is clearly visible in the MRI long-axis view, as this shows both LA and LV. Two endpoints of this valve define the MV points. A line connecting the MV points (base plane) is crucial for LV volume measurement.

RV insert (RVI) points: Two intersections between LV and RV in short-axis view defining the septum are usually marked as RVI points. The RVI points are important for 3D cardiac modeling, particularly for biventricular models.

Base-to-apex central axis points (BCA and ACA): Base and apex central axis points are essential to define the LV central axis for 3D LV models. For each patient study, one central point at a basal slice and one central point at apical slice were needed. Both were defined at the middle of the LV cavity on short-axis MRI.

A. Pre-Processing and Implementation Details

The input image size was normalized to 256×256 as per the network requirement. Images were zero-padded that were less than this size and boundaries were cropped if the size was more. The pixel values were normalized between [0,1]. To increase the training samples and reduce storage dependency, on-the-go elastic, luminance, rotation, and flip augmentation are applied. MR image analysis of the method 200 was implemented using Tensorflow and OpenCV. In the generator network, the encoder used had a kernel size of 3×3 with a depth of 4 and stride of 2. He-Normal kernel initializer was used with leaky-relu activation and batch normalization. The decoder had a stride of 1. As the GAN generates a single image with N heatmaps for N landmarks, the last layer was modified to have a single filter and stride of 1 with no activation function. The discriminator network used 2D convolution with a depth of 6 and provides an output of patch size 4×4. Both networks used Adam optimizer with a starting learning rate of 2e−4 and a starting dropout value of 0.4 for the generator and 0.6 for the discriminator network, which got dynamically adjusted during training. The discriminator network was made more dynamic by giving a higher dropout to avoid mode collapse, a common problem while training GAN. Also, a low dropout to the generator helps in convergence and avoids the vanishing gradient problem.

B. Performance Analysis

Figure 7:
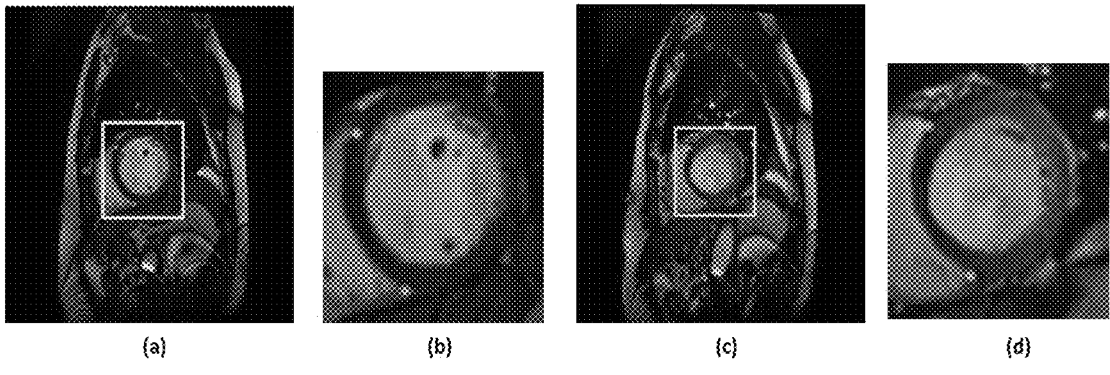
FIGS. 7 and 8 depict example diagrams of the MR image analysis by the system of FIG. 1, in accordance with some embodiments of the present disclosure.
Figure 8:
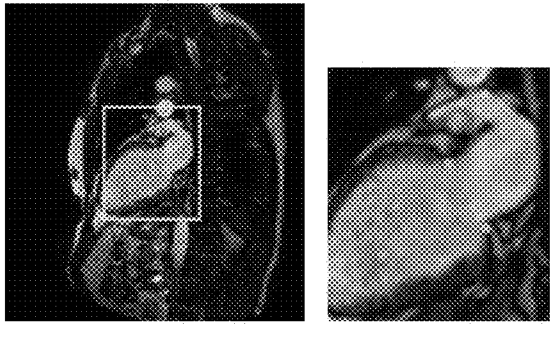

The GAN was trained using varied sample numbers. ACA and BCA had 80 samples, RVI had 542, and MV had 5142 samples. Around 80% of the data was used for training and the remaining for testing. The number of epochs used for training also varied with 1500 epochs for ACA and BCA, 1000 for RVI, and 500 epochs for MV. For detecting multiple landmarks of N heatmaps for N landmarks in a single image, circular contours were found around the heatmap. Then by considering the radius or center of the contour, landmark coordinates were localized, thus generalizing it to any number of landmarks. Euclidean distance between the predicted landmark and the actual landmark was used to calculate the error measures. It was observed that the GAN, using the method 200, predicted landmarks very close to associated ground truth data, with the error around 1 pixel as shown in FIG. 7.

It can be seen from the Table I that the performance of the method 200 on the test data is better than considered other approaches. The method 200 provided an average mean error of about 1.8 pixels for ACA, 1.6 pixels for BCA, 2.8 pixels for RVI, and 3.0 pixels for MV, performing better across all landmarks with significant improvements than the considered other approaches. The results were found to be consistent even across varied sample sizes.

TABLE I

Average error measures (in pixels) for landmark detection on training datasets. Figures indicate mean and standard deviation

| | ACA | BCA | MV | RVI |
|---|---|---|---|---|
| Mahapatra [5] | 2.2 ± 1.2 | 3.0 ± 1.6 | 9.3 ± 2.5 | 7.4 ± 2.6 |
| Lu [6] | — | 6.2 ± 4.0 | 3.5 ± 5.6 | 7.9 ± 11.5 |
| Proposed | 1.8 ± 1.2 | 1.6 ± 1.5 | 3.0 ± 1.4 | 2.8 ± 1.5 |

C. Blind-Testing on ACDC Dataset

The GAN of the system 100 was blind-tested on ACDC data, which consisted of short-axis CMR images from 100 patients with normal anatomy and pathological cases. The RVI landmarks were manually added as circular regions of 5 pixels by Sven et. al. It can be seen in FIG. 8 that the method 200 predicted the landmark points within this circular regions consistently for all tested images. To compute the error, a centre point of the circular region was considered as ground truth (GT) landmark. By comparing the predicted point with this GT landmark, the system 100 obtained an average mean error of 2.3 pixels with a standard deviation of 1.8 pixels when tested on 1000 images with varied pathologies.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address unresolved problem of landmark detection in MR image analysis. The embodiment, thus provides a method and system for MR image analysis using a GAN network. Moreover, the embodiments herein further provide a Foreground Pixel Loss (FPL) based approach by a discriminator network of the GAN, for predicting patches in an input data as one of real and fake.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method, comprising:

receiving, via one or more hardware processors, one or more Magnetic Resonance (MR) images, as a first input data, by a Generative adversarial network (GAN), wherein the one or more MR images may comprise images with or without anomalies;

performing, via the one or more hardware processors, pre-processing of the first input data to generate a pre-processed data;

performing dynamically, via the one or more hardware processors, a 3D data augmentation on the pre-processed data, to generate an augmented data;

obtaining, via the one or more hardware processors, a heatmap of a plurality of landmarks in the one or more MR images, by processing the augmented data using a generator network of the GAN;

feeding, via the one or more hardware processors, value of a Foreground Pixel Loss (FPL) function, and a second input data to a discriminator network of the GAN, wherein the second input data comprises a) an original image and the obtained landmark heatmap from the generator network, and b) the original image and an associated ground-truth heatmap;

updating, via the one or more hardware processors, gradients of the discriminator network based on value of a Modified Discriminator Loss (MDL), wherein the MDL is obtained as a combination of the FPL and a Standard Discriminator Loss (SDL) of the discriminator network;

identifying, via the one or more hardware processors, one or more patches in the obtained landmark heatmap, as associated with the ground-truth heatmap, based on the updated gradients, using the discriminator network; and predicting, via the one or more hardware processors, each of a plurality of patches in the second input data as one of real and fake, using the discriminator network, based on the one or more patches in the obtained landmark heatmap identified as associated with the ground-truth heatmap.

2. The method of claim 1, wherein performing the pre-processing of the first input data comprises performing a) an image orientation normalization, b) generating a single gaussian heatmap image for each of the plurality of landmarks, c) normalizing by applying zero padding, d) normalizing pixel values, and e) generating a heatmap image comprising all of the plurality of landmarks.

3. The method of claim 1, wherein the generator network comprises of an encoder and a decoder with a plurality of skip connections along with a feature-filter enhancing block, wherein, a plurality of key features of each of the one or more MR images is represented as vectors in latent space by the encoder, a plurality of up-sampled vectors in a decoder path are concatenated with symmetrically opposite output vector in an encoder path along a channel axis, using the plurality of skip connections, a plurality of features from a down-sampled encoder layer are concatenated using the feature-filter enhancing block, and a heat map comprising of a pixel spread normalized in a defined range is generated.

4. The method of claim 1, wherein a generative loss of the generator network is represented as $$G_L = A_L + \beta * L_L,$$

where, $A_L$ is an adversary loss, $\beta$ is an intensity parameter, and $L_L$ is a learning loss.

5. The method of claim 4, wherein the learning loss is computed as $$L_L = Huber(GT_h, GP_h, \delta = 0.4),$$

where, $GP_h$ is the heatmap obtained by the generator network, and $GT_h$ is the ground-truth heatmap.

6. The method of claim 1, wherein the foreground pixel loss function is computed as $$FPL = \propto * MSE(P_1, P_2) + MAE(P_1, P_2),$$

where, $P_1$ is a ground truth patch, $P_2$ is a predicted patch, $\propto$ is a regularization parameter, MAE is Mean Absolute Error, and MSE is Mean Square Error.

7. The method of claim 1, wherein the discriminator network comprises of a plurality of sequentially arranged 2D convolution layers.

8. The method of claim 1, wherein the value of the FPL function is obtained by:

identifying, via the one or more hardware processors, one or more foreground pixel regions in the ground-truth heatmap, wherein the one or more foreground pixel regions are patches having coverage of foreground pixels exceeding a threshold of coverage, in the ground-truth heatmap; and calculating, via the one or more hardware processors, value of the foreground pixel loss function, for the identified one or more foreground pixel regions in the ground-truth heatmap.

9. A system, comprising:

one or more hardware processors;

a communication interface; and a memory storing a plurality of instructions, wherein the plurality of instructions cause the one or more hardware processors to:

receive one or more Magnetic Resonance (MR) images, as a first input data, by a Generative adversarial network (GAN), wherein the one or more MR images may comprise images with or without anomalies;

perform pre-processing of the first input data to generate a pre-processed data;

perform dynamically, a 3D data augmentation on the pre-processed data, to generate an augmented data;

obtain a heatmap of a plurality of landmarks in the one or more MR images, by processing the augmented data using a generator network of the GAN;

feed value of a Foreground Pixel Loss (FPL) function, and a second input data to a discriminator network of the GAN, wherein the second input data comprises a) an original image and the obtained landmark heatmap from the generator network, and b) the original image and an associated ground-truth heatmap;

update gradients of the discriminator network based on value of a Modified Discriminator Loss (MDL), wherein the MDL is obtained as a combination of the FPL and a Standard Discriminator Loss (SDL) of the discriminator network;

identify one or more patches in the obtained landmark heatmap, as associated with the ground-truth heatmap, based on the updated gradients, using the discriminator network; and predict each of a plurality of patches in the second input data as one of real and fake, using the discriminator network, based on the one or more patches in the obtained landmark heatmap identified as associated with the ground-truth heatmap.

10. The system of claim 9, wherein the one or more hardware processors are configured to perform the pre-processing of the first input data by performing a) an image orientation normalization, b) generating a single gaussian heatmap image for each of the plurality of landmarks, c) normalizing by applying zero padding, d) normalizing pixel values, and e) generating a heatmap image comprising all of the plurality of landmarks.

11. The system of claim 9, wherein the generator network comprises of an encoder and a decoder with a plurality of skip connections along with a feature-filter enhancing block, wherein, a plurality of key features of each of the one or more MR images is represented as vectors in latent space by the encoder, a plurality of up-sampled vectors in a decoder path are concatenated with symmetrically opposite output vector in an encoder path along a channel axis, using the plurality of skip connections, a plurality of features from a down-sampled encoder layer are concatenated using the feature-filter enhancing block, and a heat map comprising of a pixel spread normalized in a defined range is generated.

12. The system of claim 9, wherein a generative loss of the generator network is represented as $$G_L = A_L + \beta * L_L,$$

where, $A_L$ is an adversary loss, β is an intensity parameter, and $L_L$ is a learning loss.

13. The system of claim 12, wherein the one or more hardware processors are configured to compute the learning loss as $$L_L = Huber(GT_h, GP_h, \delta = 0.4),$$

where, $GP_h$ is the heatmap obtained by the generator network, and $GT_h$ is the ground-truth heatmap.

14. The system of claim 9, wherein the one or more hardware processors are configured to compute the foreground pixel loss function as $$FPL = \propto * MSE(P_1, P_2) + MAE(P_1, P_2),$$

where, $P_1$ is a ground truth patch, $P_2$ is a predicted patch, $\propto$ is a regularization parameter, MAE is Mean Absolute Error, and MSE is Mean Square Error.

15. The system of claim 9, wherein the discriminator network comprises of a plurality of sequentially arranged 2D convolution layers.

16. The system of claim 9, wherein the one or more hardware processors are configured to obtain value of the FPL function by:

identifying one or more foreground pixel regions in the ground-truth heatmap, wherein the one or more foreground pixel regions are patches having coverage of foreground pixels exceeding a threshold of coverage, in the ground-truth heatmap; and calculating value of the foreground pixel loss function, for the identified one or more foreground pixel regions in the ground-truth heatmap.

17. One or more non-transitory machine-readable information storage mediums comprising one or more instructions which when executed by one or more hardware processors cause:

receiving one or more Magnetic Resonance (MR) images, as a first input data, by a Generative adversarial network (GAN), wherein the one or more MR images may comprise images with or without anomalies;

performing pre-processing of the first input data to generate a pre-processed data;

performing dynamically a 3D data augmentation on the pre-processed data, to generate an augmented data;

obtaining a heatmap of a plurality of landmarks in the one or more MR images, by processing the augmented data using a generator network of the GAN;

feeding value of a Foreground Pixel Loss (FPL) function, and a second input data to a discriminator network of the GAN, wherein the second input data comprises a) an original image and the obtained landmark heatmap from the generator network, and b) the original image and an associated ground-truth heatmap;

updating gradients of the discriminator network based on value of a Modified Discriminator Loss (MDL), wherein the MDL is obtained as a combination of the FPL and a Standard Discriminator Loss (SDL) of the discriminator network;

identifying one or more patches in the obtained landmark heatmap, as associated with the ground-truth heatmap, based on the updated gradients, using the discriminator network; and predicting each of a plurality of patches in the second input data as one of real and fake, using the discriminator network, based on the one or more patches in the obtained landmark heatmap identified as associated with the ground-truth heatmap.

* * * * *